United States Patent [19]

Proskow

[11] 4,051,161
[45] Sept. 27, 1977

[54] ULTRAVIOLET SCREENING AGENTS AND COATING MATERIALS CONTAINING ORGANOSILANE ESTER GROUPS

[75] Inventor: Stephen Proskow, Wilmington, Del.

[73] Assignee: E. I. Du Pont de Nemours and Company, Wilmington, Del.

[21] Appl. No.: 575,795

[22] Filed: May 8, 1975

Related U.S. Application Data

[63] Continuation of Ser. No. 289,459, Sept. 15, 1972, abandoned.

[51] Int. Cl.² .................... C07F 7/08; C07F 7/18
[52] U.S. Cl. .................. 260/448.8 R; 260/448.2 B; 260/250 R; 106/287 SB; 544/180
[58] Field of Search ............... 260/448.2 B, 448.8 R

[56] References Cited

U.S. PATENT DOCUMENTS 3,595,974   7/1971   Lloyd et al. .............. 260/448.2 B Primary Examiner—Paul F. Shaver

[57] ABSTRACT

Monomers of the formulas $R^2(O\text{-}CH_2CH(OH)(R)_a\text{-}Si(OR^1)_3)_b$ and

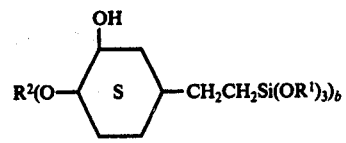

wherein R and $R^1$ are generally lower hydrocarbyl groups, $R^2$ is an aromatic ultraviolet light-absorbing moiety bonded by aromatic carbon, $a$ is 0 or 1 and $b$ is 1 or 2 are useful in the formulation of light- and abrasion-resistant coatings for polymers.

11 Claims, No Drawings

ULTRAVIOLET SCREENING AGENTS AND COATING MATERIALS CONTAINING ORGANOSILANE ESTER GROUPS

CROSS REFERENCE TO RELATED APPLICATION

This is a continuation of copending application Ser. No. 289,459, filed Sept. 15, 1972, now abandoned.

BACKGROUND OF THE INVENTION

1. Field of the Invention

This invention relates to, and has as its principal objects provision of, novel ultraviolet-absorbing agents containing organosilane ester groups useful to provide light- and scratch-resistant coatings, particularly for plastics, the novel coating solutions and coatings produced, and the coated articles, especially those made from polycarbonates, resulting from the coatings.

2. Description of the Prior Art

Many polymers, especially polycarbonates, are deficient in weatherability due to adverse effects of ultraviolet (UV) light, which causes yellowing and surface degradation and lack of abrasion resistance. Compatible coatings containing polysilicic acid as described in U.S. Pat. No. 3,429,845 have been found useful in increasing resistance to scratching but they may lack adhesion to some plastics, particularly on exposure. Incorporation of ultraviolet light absorbers has not been effective due to their loss by migration, volatilization and leaching during curing and/or exposure of the coating.

A polymeric ultraviolet absorber has been suggested in U.S. Pat. No. 3,340,231 and 3,341,493 wherein an epoxy monomer such as an unsaturated glycidyl ester is reacted with 2,4-dihydroxybenzophenone and its resulting monomer used in copolymerization with vinyl halides to give improved resistance to light. However, it is generally incompatible with useful solvents and polymer surfaces.

A further method for obtaining improved properties is suggested in U.S. Ser. No. 234,995, filed Mar. 15, 1972, wherein a copolymer of tetrafluoroethylene with a vinyl ether containing an ultraviolet-absorbing moiety is employed to give light-resistant coatings.

It is also known that polycarbonate or acrylate surfaces can be improved by the use of 2-hydroxy-4-methoxybenzophenone with mixtures of aliphatic and aromatic silanes as shown by U.S. Pat. No. 3,451,838. However, further improvements in abrasion resistance, compatibility, availability, stability and ease of application are desired.

SUMMARY OF THE INVENTION

In accordance with the present invention, there are now provided: novel silicon-containing compounds, which are useful as UV-absorbers, and their preparation; novel coating solutions formed when the novel silicon-containing compounds are added to known solutions such as those of U.S. Pat. No. 3,429,845 and a coating process using the same; and novel coatings and coated objects, especially those made from polycarbonates, produced when preformed objects are coated from the solutions.

The novel silicon-containing compounds useful as UV-absorbers, which are the basis of the invention, have one of the formulas

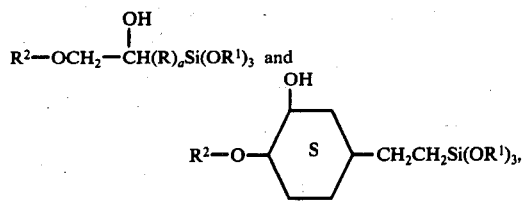

wherein:
R is a divalent hydrocarbon radical which may contain ether linkages;
$R^1$ is a lower hydrocarbon radical or $(CH_2CH_2O)_nZ$ where n is an integer of 1–8 and Z is a lower alkyl;
$R^2$ is a stable aromatic radical joined to oxygen through an aromatic carbon, with the $R^2$ group absorbing light in the region of 2500–4000A; and
a is 0 or 1.

Other details of these novel compounds as well as of other aspects of the invention will be evident in what follows.

DETAILED DESCRIPTION OF THE INVENTION

The new silicon-containing compounds having ultraviolet-absorbing moieties as represented by the above formulas are obtained by reaction of an epoxy silane with a hydroxyl group of a hydroxy-aromatic UV-absorber and will be referred to in this specification as "adducts."

The epoxysilicone compounds or epoxysilanes employed in the reaction with a hydroxy-aromatic UV-absorber have been described in U.S. Pat. No. 2,946,701. They have the formulas

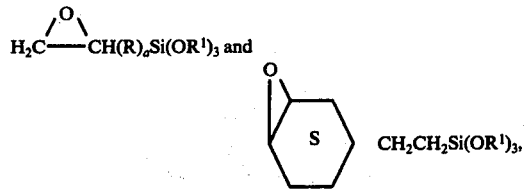

R is a divalent hydrocarbon radical of less than 10 carbon atoms, or a divalent radical of less than 10 carbon atoms composed of C, H and O atoms, the last being in the form of ether linkages (and preferably R is $-CH_2OCH_2CH_2CH_2-$);
$R^1$ is an aliphatic hydrocarbon radical of less than 5 carbon atoms, an acyl radical of less than 5 carbon atoms or a radical of the formula $(CH_2CH_2O)_nZ$ in which n is an integer of at least 1 and Z is an aliphatic hydrocarbon radical of less than 5 carbon atoms; and
a is 0 or 1.

The preparation of illustrative compounds is shown in the above-mentioned U.S. Pat. No. 2,946,701. Particularly preferred compounds are those in which $R^1$ is methyl, available commercially as Union Carbide A-187 and A-186, i.e., α-glycidoxypropyltrimethoxysilane and α-(3,4-epoxycyclohexyl)ethyltrimethoxysilane.

The precursor hydroxyaromatic UV-absorbers include the principal classes of commercial ultraviolet-screening agents, i.e., benzophenones, benzotriazoles, salicylates, substituted quinazolines and phenyltriazines. All these generally absorb light in the range 2500–400-

0A and dissipate the UV-radiation into harmless energy. The requirements for effective absorption are shown in "Stabilization of Polymers and Stabilizer Processes" Advances in Chemistry, Series 85, Am. Chem. Soc. Washington, D.C. 1968, p. 284 and H. J. Heller "Protection of Polymers Against Light Radiation" European Polymer Journal — Supp. 1969 Pergamon, England, p. 105–132.

A formula for these precursors may be written as $R^2(OH)_b$, where $b$ is 1 or 2 depending on the number of hydroxyls reacted. $R^2$, which absorbs light as noted, is a hydroxy-aromatic radical containing up to 4 aromatic rings, and preferably 2–4 aromatic rings. It generally has a molecular weight of at least 151 (structure 2 below, $p = 1$) and usually less than 325 (unsubstituted; structure 13). In structure 8, as illustrated by Examples 2 and 3, below, $R^2$ is viewed as bonded to two silane groups (i.e., as $R^2(OH)_b$ where $b$ is 2). Substituents present on the rings may increase the molecular weight to about 400.

Particularly useful UV-absorbing structures representative of $R^2$ are shown by the following formulas:

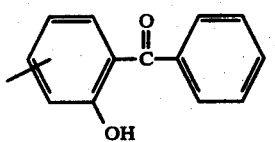

1.

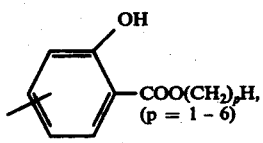

2.

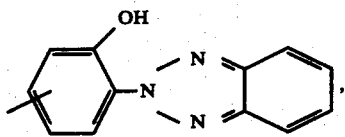

3.

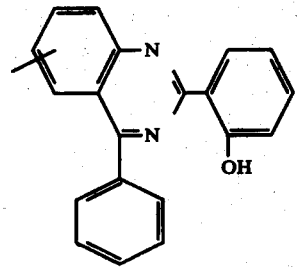

4.

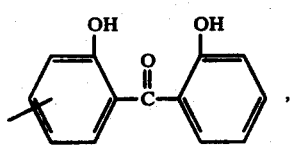

5.

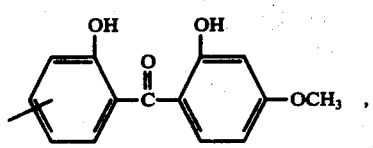

6.

7.

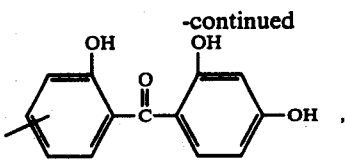

8.

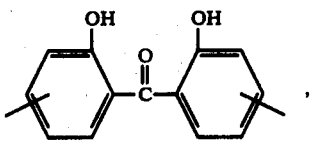

9.

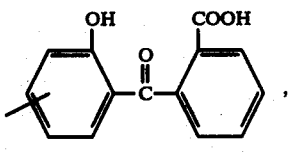

10.

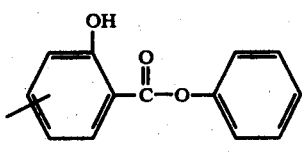

11.

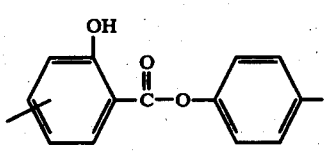

12.

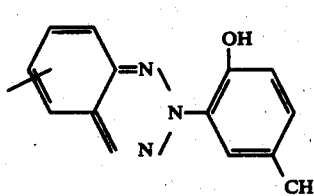

, and

13.

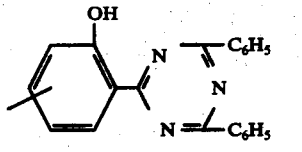

Any of these structures may optionally have up to 2 inert substituents, such as halogen, alkyl, phenyl, alkoxy on nuclear carbon. Generally preferred are groups of the above formulas wherein the bonding is in the para position.

A particularly useful precursor hydroxy-aromatic compound is that corresponding to the first structure listed, i.e., 2,4-dihydroxybenzophenone. Particularly useful specific hydroxyaromatic compounds in addition to those of Examples 1 and 2, below, are 2,4-dihydroxybenzoate, 2-(2'-hydroxyphenyl)-4-phenyl-6-hydroxyquinazoline and 2-(2',4'-dihydroxyphenyl)benzotriazole.

Process conditions for the reaction between the precursor silanes and hydroxyaromatic compounds are simple. The compounds are merely contacted under anhydrous conditions in the presence of an alkali quaternary ammonium salt, generally at 50°–125° for a period of 4–10 hours. A diluent or solvent is not required but can be used if desired.

The novel adducts produced are generally viscous liquids soluble in polar organic solvents such as lower aliphatic alcohols, lower aliphatic ketones, acetonitrile, lower aliphatic esters such as ethyl acetate, dioxane, furane, dimethyl sulfoxide, and dimethylformamide.

The adducts are particularly suited for use in coating solutions and coatings mixed with polysilicic acid and copolymers as taught in U.S. Pat. No. 3,429,845. For this purpose, the silicic acid present can range from about 10% to about 90% of the weight of the composition, preferably from about 20% to about 50%, the percentage in each case being calculated as silica. The polysilicic acid is prepared by hydrolyzing tetraethylsilicate in a mixture of ethyl alcohol and water, or preferably 0.1N hydrochloric acid, in the ratio of about 5:1 to 2:1, preferably about 3-4:1.

The copolymers employed in the coating solution are hydroxylated fluorocopolymers, preferably copolymers of tetrafluoroethylene with an ω-hydroxyalkyl vinyl ether wherein the hydroxyl is primary and the alkyl is of 2-6 carbons. These copolymers are formed from alternating units and hence have a 1:1 molar ratio. Less preferred are copolymers wherein at least some of the tetrafluoroethylene is replaced by chlorotrifluoroethylene or where hydroxyls are secondary as in hydrolyzed copolymers of the fluoro-olefin with vinyl esters. These are further described in U.S. Pat. Nos. 3,429,845 and 3,429,846.

Although the silicic acid variation of the invention, above, is preferred as imparting good scratch-resistance, a coating mixture of a hydroxylated fluoropolymer and a hexa(alkoxyalkyl)melamine ("alkoxy" containing up to 8 carbons), e.g., hexa(methylmethyl)melamine, of the type taught in U.S. Pat. No. 3,651,003 can be employed. In this variation, up to 45% by weight of the fluoropolymer can be replaced by the melamine. Of course, silica itself can be used with these components, also as taught by U.S. Pat. No. 3,651,003.

To effect the improvement in coatings obtained by this invention, between about 0.5 and 35% by weight, based on the combined weight of the polysilicic acid (calculated as silica) and/or hexa(alkoxyalkyl)melamine and copolymer, of one of the novel adducts described above is simply included in the coating solution. More than one adduct can, of course, be employed, sometimes to advantage.

Solvents for the above, and possibly other minor ingredients, are employed which are compatible in a wide range of proportions and which generally have appreciable vapor pressure at about 100° C. Useful are lower alkanols, mixtures of alkanols with lower alkanoic acids, and/or with lower aliphatic ketones. Minor amounts of ether alcohols (Cellosolve®), esters, aromatic hydrocarbons and water can be present. Enough solvent is generally employed to give a desirable solution viscosity (see below), but quantity is not critical.

Long shelf life of the coating solution is attained if a compound reactant with any residual epoxy groups, e.g., an alcohol such as n-butanol, is added to the epoxy-containing silane/ultraviolet-absorber mixture after the reaction between the constituents of the latter is substantially complete (see Example 6B, below) to prevent reaction of any epoxy groups present with polymers of the coating solution. Since these compounds are good solvents, they can be readily employed as such and simultaneously stabilize the solution.

In addition to the above, there may be included in the solution optional and minor amounts of:

1. Organo-silicone compounds that are block copolymers of lower alkylene (2-4 carbon) oxides with lower dialkyl siloxanes employed in an amount of 0.05-5% based on the weight of polysilicic acid (calculated as $SiO_2$) present. These are further described in U.S. Pat. No. 2,476,827;

2. Salts such as potassium thiocyanate and including sodium thiocyanate, and sodium or potassium carboxylates in an amount of 0.025 to 2% based on the total weight of polysilicic acid (as $SiO_2$) and copolymer (e.g., of tetrafluoroethylene and hydroxyalkyl vinyl ether). These are further described in U.S. Pat. No. 3,390,203; and 3. Polyethers having a macrocyclic ring of at least 14 atoms including at least 4 ring oxygens as described in U.S. Pat. No. 3,546,318. These can be employed in amounts of 0.01-5% based on the total weight of polysilicic acid (as $SiO_2$) and copolymer.

The coating solutions have a solids content (substantially nonvolatile components of polysilicic acid or equivalent and fluoropolymer and possible minor amounts of (1), (2) and (3) above) of 2-25%. Although the proportion of hydroxyl and fluorine-containing polymer to polysilicic acid (as $SiO_2$) can be from 10-90 to 90-10, usually 80-50 to 20-50 is present. The coating solution generally has a viscosity of about 10-50 cps (room temperature) or even up to 300 cps, low viscosities being used to give thin coatings and higher (30 or more) to give thicker coatings. For storage or shipping, higher viscosities, e.g., 100-300 cps, may be preferred.

Overall proportions in compositions of coating solutions useful in this invention are given in the following table (in which percentages are by weight):

| COATING SOLUTION COMPOSITION | | |
|---|---|---|
| | Ranges (Calcd. on Solids | |
| Major Constituents | Useful (%) | Preferred % |
| Polysilicic acid (as $SiO_2$) and/or melamine | 90-10 | 50-20 |
| Copolymer | 10-90 | 50-80 |
| Adjuvants (as % of fluoropolymer and polymers) | | |
| Adduct of invention | 0.5-35 | 5-15 |
| Organosilicone | 0-4.5 | 0.05-2.5 |
| Alkali metal salt | 0-2 | 0.025-2 |
| Polycyclic polyether | 0-5 | 0.01-5 |
| Solvent | | |
| To give solution viscosity of 10-300 cps (10-50 preferred for use) | | |

The coating solutions are useful to produce light- and scratch-resistant coatings on metals, polymers, woods, etc. and applied to the substrate by conventional solution coating techniques such as flowing, spraying, dipping and the like. Contact time between coating solution and substrate, e.g., rate of withdrawal from a bath, is, of course, a factor influencing the thickness of the resultant coating. The compositions are finally dried and preferably baked, the maximum baking temperature being maintained below about 200° C. In general, time and temperature are interdependent, i.e., periods of 1 hour at 170°-180° C, 5-16 hours at 120°-130° C are employed. The baking or curing gives hard surfaces and adherent coatings.

Very thin coatings (0.1μ) of the present invention can be employed but, in general, coatings of about 3-20μ (3-7μ are usually preferred) give excellent ultraviolet protection to the substrate. In particular, excellent adhesion is obtained when the polymers are employed with polysilicic acid to give abrasion-resistant coatings. Furthermore, the ultraviolet-absorbing property is retained during the baking operation which generally tends to eliminate low molecular weight protective agents by volatilization or migration. It may be noted that solid materials of the present invention (formed by evaporation of solvent) are self-supporting and can be used alone, e.g., to produce molded objects.

It appears that the trialkoxysilane groups, —Si(OR')₃, of the present adducts probably hydrolyze in the coating solution during application and condense to form a polymeric material, or complex, with polysilicic acid and/or a hydroxyl-containing polymeric substance such as TFE/HBVE copolymer. During the hydrolysis, aging and curing processes, the ultraviolet-screening moiety becomes an integral part of the abrasion-resistant coating material with subsequent superior properties due to nonvolatility and lack of ability for migration. The ultimate structure of these polymeric coatings, or complexes, probably consists of coextensive compatible structures of a tough linear polymer chemically bonded, hydrogen bonded and/or mechanically entwined with a hard three-dimensional

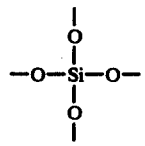

network on which there remain some silanol groups.

EMBODIMENTS OF THE INVENTION

There follow several nonlimiting examples illustrating various aspects of the invention. Examples 1–3 show novel adducts and Examples 4 and 5, coatings on quartz and poly(methyl methacrylate), respectively. Example 6 shows an adduct in a coating solution used to coat the preferred polycarbonate. In these examples, parts and percentages of materials are by weight unless otherwise specified. Abbreviations used include: TFE for tetrafluoroethylene; HBVE for 4-hydroxybutyl vinyl ether; and PMMA for poly(methyl methacrylate).

EXAMPLE 1

2,4-Dihydroxybenzophenone/γ-Glucidoxypropyltrimethoxysilane 1:1 Adduct

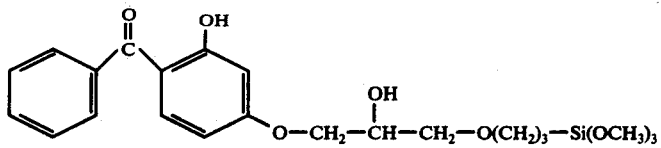

The above compound (Adduct I, was prepared by heating a mixture of 10.7 g (0.05 mole) of 2,4-dihydroxybenzophenone and 12.04 g (0.051 mole) of γ-glycidoxypropyltrimethoxysilane under nitrogen in the presence of 0.1 g of tetramethylammonium chloride. The mixture was stirred and gradually heated to 75°–80° C, then maintained at this temperature for 8 hours. During this period it changed into a homogeneous, viscous oil. An equivalent product was obtained when the reactants were heated to 80° C for 4 hours.

Coatings prepared as in Example 4 but applied to polycarbonate and cured 60 min at 130° C could not be stripped from this substrate by the adhesive tape pull test.

EXAMPLE 2

2,2',4,4'-Tetrahydroxybenzophenone/γ-Glycidoxyproplytrimethoxysilane 1:2 Adduct

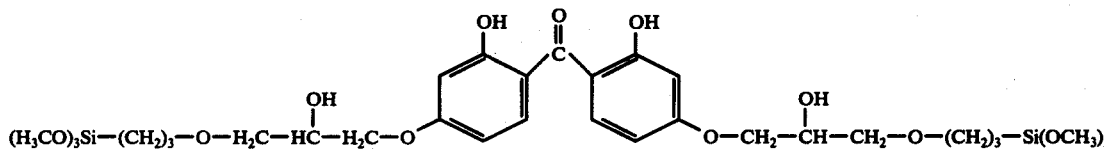

The general procedure of Example 1 was used to react 4.92 g (0.02 mole) of 2,2',4,4'-tetrahydroxybenzophenone with 9.44 g (0.04 mole) of the epoxysilane of Example 1 to give the above Adduct II. After the addition of 0.1 g of tetramethylammonium chloride, the mixture was heated 6 hr at 75°–80° C. A clear, slightly reddish yellow oil was obtained and was evaluated in 27/73-SiO₂/TFE-HBVE coatings on PMMA without further purification.

A coating applied to polycarbonate and cured 60 min at 130° could not be stripped from this substrate by the adhesive tape pull test.

EXAMPLE 3

2,2',4,4'-Tetrahydroxybenzophenone/β-(3,4-epoxycyclohexyl)ethyltrimethoxysilane 1:2 Adduct

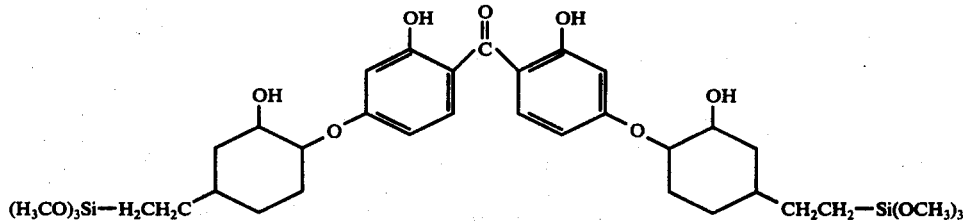

The above Adduct III was prepared by heating 2,2',4,4'-tetrahydroxybenzophenone (4.92 g, 0.02 mole) at 80° C with 9.84 g (0.04 mole) of β-(3,4-epoxycyclohexyl)ethyltrimethoxysilane and 0.1 g of tetramethylammonium chloride. A pale, reddish-brown, viscous oil was obtained.

EXAMPLE 4

Optical Density Of Coatings On Quartz

Coating solutions containing about 10 wt % (based on solids) of the novel silanes of Examples 1-3 with about 10% polysilicic acid $(SiO_2)$/TFE-HBVE at a weight ratio of 27/73 of $SiO_2$/copolymer in n-butanol/t-butanol as solvent were coated onto quartz plates (transparent to UV radiation), and the solvent removed by evaporation. A PMMA sheet was placed directly over the layer and heated for 60 minutes at 170° C. The following table shows the percent loss in optical density of the coating on quartz at 2800-3500A by volatilization and migration to the PMMA sheet.

Table 1

| UV-Absorber | % Loss of Optical Density | |
|---|---|---|
| | By Volatilization | By Migration |
| Adduct I | 37 | 0 |
| Adduct II | 25 | 2 |
| Adduct III | 13 | 23 |
| 2,4-Dihydroxybenzophenone* | 90 | not determined |
| 2,2',4,4'-Tetrahydroxy-benzophenone* | 13 | 85 |

*Applied at 5% instead of 10%

EXAMPLE 5

Coatings on poly(methyl methacrylate)

Coatings containing 10 and 15 wt percent (based on total solids in the coating solution) of Compounds I and II in a solution of about 10% of polysilicic acid/TFE-HBVE in a mixture of n- and t-butyl alcohol solvent were applied to PMMA surfaces as described in U.S. Pat. No. 3,429,845 and the preceding examples with a curing time of 1 hour at 170° C. The following table shows results obtained as compared to a coating of the copolymer without added ultraviolet-absorbing agents. Note particularly the improvement in adhesion retention.

Table 2

| Ultraviolet Absorber | Adduct I | Adduct I | Adduct II | Control |
|---|---|---|---|---|
| Amount wt % | 10 | 15 | 10 | 0 |
| Coating thickness (μ) | 5.0 | 4.8 | 5.2 | 6.9 |
| Optical Density A | | | | |
| 3210 | 0.8 | 1.2 | 1.1 (3520) | not det. |
| 2880 | 1.2 | 1.8 | 0.9 | not det. |
| 2420 | 0.9 | not det. | not det. | not det. |
| Adhesion (%) | 100 | 100 | 100 | 100 |
| Adhesion after exposure to 2537A (hrs) | 100(6) 90(24) 10(27) | 100(6) 98(54) 40(60) | 90(30) 70(42) 0(45) | 99(3) 0(6) |

EXAMPLE 6

1:1 Product of 2,4-dihydroxybenzophenone and γ-glycidoxypropyltrimethoxysilane in Coating in Polycaronates Part A In essentially the procedure of Example 1, a dry 12-liter, 3-necked, round-bottom flask equipped with stirrer, thermometer, reflux condenser and nitrogen inlet was charged with 1796 g (7.6 moles) of γ-glycidoxypropyltrimethoxysilane, 1628 g (7.6 moles) of 2,4-dihydroxybenzophenone, and 15 g of tetramethylammonium chloride. With heating and stirring, the 2,4-dihydroxybenzophenone was dissolved at a pot temperature of 60°-80° C. Heating and stirring were continued at an initial temperature of 110°-116° C. After 1 hours, the mixture became viscous, and a slow reflux developed. Heating was continued for a total of 5 hours, at the end of which time the pot temperature was 101° C. n-Butanol (5136 g) and 15 g of tetramethylammonium chloride were added, and the mixture was heated under reflux for two additional hours. After cooling overnight, the clear brown solution was discharged under nitrogen into dry containers and sealed. The solution (8538 g) contained approximately 40% of Adduct I.

Part B

1. A first coating solution was prepared as follows:
   85 lbs. of a solution of polysilicic acid in ethanol (obtained by mixing 65 lbs of an approximately 70% solution of tetraethylorthosilicate in ethanol and 20 lbs. of 0.1 N aqueous hydrochloric acid. This mixture was aged 17 hours prior to the addition of the remaining ingredients).
   315 lbs of TFE/HBVE copolymer [about 1:1 solution in mixed tert butanol/n-butanol (about 11% solids)]
   100 lbs of glacial acetic acid
   125 g of "L-520" organosilicone [which is a block copolymer of lower alkylene oxides with dimethylsiloxane (Union Carbide Co.)]
   1.6 lbs of a 10% solution of KSCN in methanol
   1.6 lbs of a 40% solution of 2,4,8,18,21-hexaoxatricyclo[20.4.0.0$^{9,14}$]hexacosane in n-butanol
   65 lbs of n-butanol The Brookfield viscosity of the coating solution was 30.8 cps at 25° C.

A total of 38.7 g of the 40% n-butanol solution of adduct as prepared in Part A was combined with 1957 g of the coating solution prepared above. After 24 hours at room temperature, the mixture had a Brookfield viscosity of 31.45 cps at 25° C. Two weeks after the original preparation the mixture was still liquid and had a Brookfield viscosity of 41.5 cps at 25° C.

2. A somewhat less stable second coating solution without excess n-butanol was prepared as follows:
   460 g of a solution of polysilicic acid in ethanol, prepared by mixing 9 parts of tetraethylorthosilicate, 4 parts of ethyl alcohol and 4 parts of 0.1N aqueous hydrochloric acid (as above)
   1700 g of TFE/HBVE copolymer solution in butanol (as above)
   540 g of glacial acetic acid
   1.6 g of "L-520" silicone (as above)
   8.5 ml of a solution of 10.2 g of KSCN dissolved to 100 ml in methanol
   8.64 g of a 40% solution of hexaoxatricyclohexacosane (as above) in n-butanol.

About 200 g of this coating solution was added to 2 g of the following addition product:
   10.7 g (0.05 mole) of 2,4-dihydroxybenzophenone, 10.7 g (0.0453 mole) of γ-glycidoxypropyltrimethoxysilane and 0.1 g of tetraethylammonium chloride were placed in a dry 200-ml, round-bottom flask and stirred under dry nitrogen at a bath temperature of 90°-100° C for a period of 6¾ hours. On cooling overnight, a viscous, brown oil resulted which was used promptly. The coating solution gelled on standing for 4 days whereas that treated with an alcohol as shown by Part B(1) was stable since residual epoxy groups were not present.

Part C

2 × 1 × ⅛ inch quartz plate was immersed in the coating solution of Part B(1). After 2 minutes, the quartz panel was withdrawn at a rate of 15 in/min. The panel was dried under nitrogen, the coating was removed from one side with a razor blade, and the ultraviolet spectrum of the quartz panel, now coated on one side only, was scanned between 2500 A and 4000 A on a Cary 14 spectrophotometer. The panel was cured in a circulating air oven for 16 hours at 135° C and the UV spectrum measured again. Table 3 summarizes the maximum absorbance (A max) at 2880A before and after curing.

In a control experiment, 2 g of 2,4-dihydroxybenzophenone was added to 200 g of the coating solution of Part B(1) which did not contain the adduct of Part A. A quartz panel was coated and the UV spectrum measured before and after curing as described above. "A max" of the dihydroxybenzophenone-containing coating before and after curing are included in Table 3. Percent ΔA max gives directly the percent loss in optical density on curing.

Table 3 larly inspected for the initial appearance of cracks or blisters, indicated by "peeling" in Table 4.

Table 4

| Accelerated Weathering of Coated Polycarbonate | | |
|---|---|---|
| Coating | 0% Adhesion-Tape Pull Hours | Peeling Hours |
| With Adduct I | 620 | 1670 |
| Control | 187 | 486 |

The UV-stabilized coated polycarbonate and the control were also exposed to accelerated outdoor weathering in Arizona. EMMA is an equatorial follow-the-sun exposure rack with mirrors. The solar radiation is increased by a factor of almost 10 over a 45° south stationary mount. EMMAQUA combines EMMA exposure with a water spray for 8 minutes every sunny hour.

The results of 12 weeks of EMMA and EMMAQUA exposure are summarized in Table 5. In addition to the adhesive tape pull test and the visual inspection for "peeling," the degree of yellowing (yellowness index, YI) was measured on a Hunter Color-Difference Meter according to ASTM D-1925.

Table 5

| | 12 Weeks Accelerated Outdoor Weathering of Coated Polycarbonate | | | | | |
|---|---|---|---|---|---|---|
| | % Adhesion-Tape Pull | | Peeling | | YI | |
| Coating | EMMA | EMMAQUA | EMMA | EMMAQUA | EMMA | EMMAQUA |
| With adduct I | 100 | 0 | No | No | .8 | .5 |
| Control | 0 | 0 | No | Yes | 15.6 | 11.6 |

| Loss of Optical Density on Curing of Ultraviolet Stabilized Coating | | | | |
|---|---|---|---|---|
| | A max | | | |
| Ultraviolet Absorber | Dry | Cured | ΔA max | % ΔA max |
| Adduct I | 0.78 | 0.67 | .11 | 14.1 |
| 2,4-dihydroxybenzophenone | 1.93 | 0.08 | 1.85 | 96 |

Part D

A 40% solution in n-butanol of Adduct I was prepared as described in Part A from 42.8 g (0.4 moles) of 2,4-dihydroxybenzophenone, 47.2 g (0.4 moles) of γ-glycidoxypropyltrimethoxysilane, two portions each of 0.4 g of tetramethylammonium chloride and 135 g of n-butanol.

A total of 67.5 g of the resulting 40% solution of addition product were added to 2719 g of a coating solution prepared as described in Part B(2). A 16 × 12 × ⅛ inch extruded polycarbonate sheet was immersed in this solution for 2 minutes and withdrawn at a rate of 15 in/min. After drying for 45 min, the coated polycarbonate panel was cured for 16 hours at 135° C. The coating thickness as determined according to the procedure in the J. Opt. Soc. Am. 37, 873 (1947) was 5.6μ.

Similarly, a non-UV-stabilized coating was applied to polycarbonate sheet from the same coating solution but without addition of the adduct. The coating thickness was 4.5μ. This panel was uses as a control for the ensuing exposure to accelerated weathering.

Both the UV-stabilized coated polycarbonate panel and the nonstabilized control were exposed to accelerated weathering in an Atlas Weather-Ometer®, Type XW. An 18 min spray of distilled water was applied during every two hours of exposure. Adhesion to polycarbonate of the coating on the exposed side was monitored by the adhesive tape pull test described in U.S. Pat. No. 3,546,318. Furthermore, the panels were regu- The embodiments of the invention in which an exclusive property or privilege is clamined are defined as follows:

1. A compound of one of the formulas

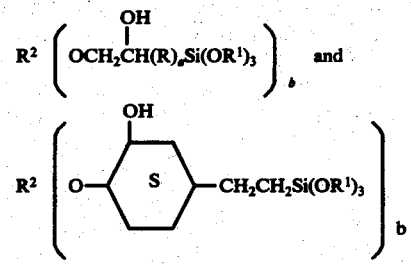

wherein
R is a divalent hydrocarbon or hydrocarbon ether radial of up to 10 carbons;
$R^1$ is an aliphatic hydrocarbon radical of less than 5 carbon atoms, an acyl radical of less than 5 carbon atoms, or a radical of the formula $(CH_2CH_2O)_nZ$ in which n is an integer of 1 to 8 and Z is an aliphatic hydrocarbon radical of less than 5 carbon atoms;
$R^2$ is a stable, monovalent or divalent carbocyclic hydroxy-aromatic radical, containing up to 4 aromatic rings joined to oxygen through an aromatic carbon, of the type which absorbs light in the region of 2500–4000 A in an amount effective for stabilizing polymers against ultraviolet light;
a is 0 or 1; and
b is 1 or 2.

2. The compound of claim 1, the 1:1 adduct of 2,4-dihydroxybenzophenone and α-glycidoxypropyltrimethoxysilane.

3. The process of preparing a compound of claim 1 which comprises reacting at least one epoxysilane of the formulas

 and

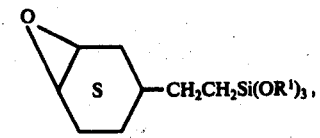

wherein
R is a divalent hydrocarbon or hydrocarbon ether radical of up to 10 carbons;
$R^1$ is an aliphatic hydrocarbon radical of less than 5 carbon atoms, an acyl radical of less than 5 carbon atoms or a radical of the formula $(CH_2CH_2O)_nZ$ in which n is an integer of 1 to 8 and Z is an aliphatic hydrocarbon radical of less than 5 carbon atoms; and
a is 0 or 1,
with a compound of the formula $R^2(OH)_b$ wherein
$R^2$ is a stable, carbocyclic hydroxy-aromatic radical, containing up to 4 aromatic ring joined to oxygen through an aromatic carbon, of the type which absorbs light in the region of 2500–4000 A in an amount effective for stabilizing polymers against ultraviolet light; and
b is 1 or 2,
under anhydrous liquid conditions in the presence of an alkyl quaternary ammonium salt.

4. The process of preparing a compound of claim 2 which comprises reacting 2,4-dihydroxybenzophenone and γ-glycidoxypropyltrimethoxysilane under anhydrous liquid conditions in the presence of an alkyl quaternary ammonium salt.

5. A compound of the formula

wherein
R is a divalent hydrocarbon or hydrocarbon ether radical of up to 10 carbons;
$R^1$ is an aliphatic hydrocarbon radical of less than 5 carbon atoms, an acyl radical of less than 5 carbon atoms, or a radical of the formula $(CH_2CH_2O)_nZ$ in which n is an integer of 1 to 8 and Z is an aliphatic hydrocarbon radical of less than 5 carbon atoms;
$R^2$ is a stable, monovalent, carbocylic hydroxyaromatic radical, containing up to 4 aromatic rings joined to oxygen through an aromatic carbon, of the type which absorbs light in the region of 2500–4000 A in an amount effective for stabilizing polymers against ultraviolet light; and
a is 0 or 1.

6. The process of preparing a compound of claim 5 which comprises reacting an epoxysilane of the formula

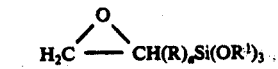

wherein
R is a divalent hydrocarbon or hydrocarbon ether radical of up to 10 carbons;
$R^1$ is an aliphatic hydrocarbon radical of less than 5 carbon atoms, an acyl radical of less than 5 carbon atoms or a radical of the formula $(CH_2CH_2O)_nZ$ in which n is an integer of 1 to 8 and Z is an aliphatic hydrocarbon radical of less than 5 carbon atoms; and
a is 0 or 1,
with a compound of the formula $R^2OH$ wherein
$R^2$ is a stable, monovalent, carbocyclic hydroxyaromatic radical, containing up to 4 aromatic rings joined to oxygen through an aromatic carbon, of the type which absorbs light in the region of 2500–4000 A in an amount effective for stabilizing polymers against ultraviolet light;
under anhydrous liquid conditions in the presence of an alkyl quaternary ammonium salt.

7. A compound of claim 1 wherein $R^2$ is selected from the group consisting of

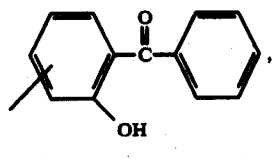

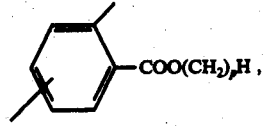

(p = 1-6)

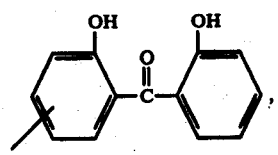

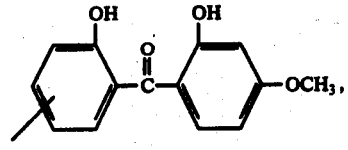

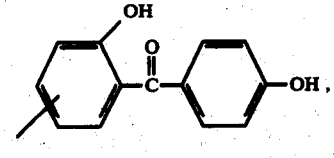

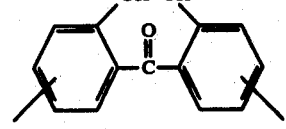

-continued

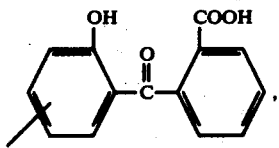,

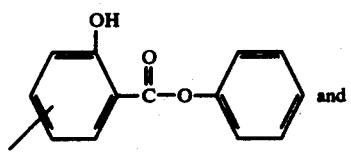 and

-continued

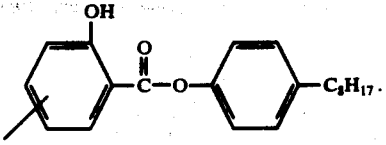.

8. The compound of claim 1, the 1:2 adduct of 2,2',4,4'-tetrahydroxybenzophenone and γ-glycidoxypropyltrimethoxysilane.

9. The compound of claim 1, the 1;2 adduct of 2,2',4,4'-tetrahydroxybenzophenone and β-(3,4-epoxycyclohexyl)ethyltrimethyloxysilane.

10. The process of preparing the compound of claim 8 which comprises reacting 2,2',4,4'-tetrahydroxybenzophenone and γ-glycidoxypropyltrimethoxysilane under anhydrous liquid conditions in the presence of an alkyl quaternary ammonium salt.

11. The process of preparing the compound of claim 9 which comprises reacting 2,2',4,4'-tetrahydroxybenzophenone and β-(3,4-epoxycyclohexyl)ethyltrimethoxysilane under anhydrous liquid conditions in the presence of an alkyl quaternary ammonium salt.

* * * * *